United States Patent [19]

Hagen

[11] Patent Number: 5,159,125
[45] Date of Patent: Oct. 27, 1992

[54] CATALYZED VAPOR PHASED PROCESS FOR MAKING ALCOHOLS

[75] Inventor: Gary P. Hagen, West Chicago, Ill.

[73] Assignee: Amoco Corporation, Chicago, Ill.

[21] Appl. No.: 815,243

[22] Filed: Dec. 23, 1991

Related U.S. Application Data

[63] Continuation-in-part of Ser. No. 702,837, May 20, 1991, Pat. No. 5,095,156, which is a continuation of Ser. No. 413,314, Sep. 27, 1989, abandoned.

[51] Int. Cl.$^5$ ............... C07C 29/32; C07C 29/34; C07C 31/12
[52] U.S. Cl. .................. 568/904; 568/697; 568/905
[58] Field of Search ................ 568/904, 905

[56] References Cited

U.S. PATENT DOCUMENTS

| | | | |
|---|---|---|---|
| 2,050,788 | 8/1936 | Fuchs et al. | 260/156 |
| 2,668,181 | 2/1954 | Banes et al. | 568/904 |
| 3,413,358 | 11/1968 | Asahara | 568/904 |
| 3,888,911 | 6/1975 | Dench et al. | 568/904 |

Primary Examiner—Joseph E. Evans
Attorney, Agent, or Firm—William H. Magidson; Robert J. Wagner; Frank J. Sroka

[57] ABSTRACT

A catalyzed, continuous vapor phase process to convert a $C_2$ or higher olefin in combination with methanol to a mixture containing at least one higher molecular weight alcohol, for example, isobutanol, over a magnesium oxide composition. The process also may contain a lower aldehyde and/or ketone in the feed.

6 Claims, No Drawings

CATALYZED VAPOR PHASED PROCESS FOR MAKING ALCOHOLS

This is a continuation-in-part of application Ser. No. 07/702,837, filed May 20, 1991, now U.S. Pat. No. 5,095,156, which in turn is a continuation of application Ser. No. 07/413,314, filed Sep. 27, 1989, now abandoned.

BACKGROUND OF THE INVENTION

This invention relates to a vapor phase process for catalytically converting two or more lower molecular weight alcohols or their dehydration products (olefins), optionally in combination with a lower molecular weight aldehyde and/or ether, to a mixture containing at least one higher molecular weight alcohol over an alkaline catalyst and, more particularly, to a vapor phase, continuous process for converting a $C_2$ or higher alcohol or olefin, in combination with methanol and, optionally, an aldehyde and/or ether, to a mixture containing at least one higher molecular weight alcohol over a catalyst which is essentially magnesium oxide.

In recent years there has been an upsurge in interest in the production of both chemicals and transportation fuels from non-petroleum carbon sources such as methane, tar sands, oil shale and the like. This interest has focused for lack of good direct conversion processes on indirect processes, which often go through a synthesis gas intermediate with subsequent conversion of the synthesis gas via Fisher-Tropsch and related processes to hydrocarbons and/or oxygenates. Oxygenates, particularly lower alcohols, are common products of such synthesis gas reactions, and high conversion, selective processes to convert an alcohol or a mixture of alcohols to higher molecular weight alcohols have substantial commercial potential.

One potential process for alcohol feeds uses the well-known, non-catalytic Guerbet reaction which converts a lower molecular weight alcohol to a branched or linear higher molecular weight alcohol in the presence of an alkali metal alkoxide dissolved in the alcohol to be converted. Such processes are uncatalyzed, moderate temperature batch reactions. When considered for industrial use, however, the Guerbet reaction suffers an economic disadvantage in that a portion of the starting alcohol (and possibly some of the product) is consumed by oxidation to the corresponding carboxylic acid unless special agents are added. One publication suggests the use of a mixture of potassium hydroxide and boric oxide to suppress acid formation which is said to improve the yield.

More recently, an improved Guerbet reaction has been reported which uses a "catalyst" system employing magnesium oxide, potassium carbonate, and copper chromite for converting, for example, ethanol to higher alcohols including 1-butanol, and 1-butanol to higher alcohols including 2-ethyl-1-hexanol (J. Org. Chem. 22, 540-2 (1957)). The reaction is of the batch type and the "catalyst" is said to have limited lifetime.

Another improvement in the Guerbet reaction, discussed in J. Mol. Catalysis 33, 15-21 (1985), uses a sodium alkoxide mixed with 5% rhodium on alumina as a "catalyst." A mixture of 1-butanol and methanol is said to be converted by the "catalyst" to a mixture of 2-ethyl-1-hexanol and 2-methyl-1-butanol.

Still other batch Guerbet reaction variations include water removal to improve yield and the use of an alkali metal hydroxide "catalyst" (U.S. Pat. No. 3,328,470), the use of an alkali metal alcoholate/boric acid ester "catalyst" (U.S. Pat. No. 2,861,110), and the addition of a nickel "catalyst" to the metal alkoxide (J. Am. Chem. Soc. 76, 52 (1953)).

Octane demand has scared in recent years and the growth is likely to continue in the United States. For example, it has been estimated that clear pool octane demand has been increasing by 0.15 units/year in recent years. The addition of alcohols and ethers such as methanol, ethanol and methyl t-butyl ether to gasoline to improve octane number and/or improve the effect of gasoline combustion in internal combustion engines on the environment has been the subject of a number of recent publications.

Methanol is generally made from synthesis gas and ethanol can be made by carbonylation of methanol or more usually from agricultural products by fermentation. Higher alcohols can also result from the catalyzed conversion of synthesis gas. Olefins such as ethylene and propylene are made in large quantities by the cracking of alkanes such as ethane, propane and naphtha. Potentially, additional large amounts of ethylene are available from natural gas by the oxidative coupling of the methane component.

Methanol, while effective if used essentially pure for transportation fuel, is not a good additive for gasoline and is also potentially available in large quantities by the partial oxidation the methane component in natural gas. Ethanol has shown promise as a gasoline additive, but isobutanol in particular is valuable as it can be dehydrated to isobutylene and reacted with methanol to form methyl t-butyl ether (MTBE) which is an excellent octane improver that can be easily blended into gasoline. Isobutanol is also an effective octane improver. The methyl ether of isopentanol (TAME) is also an excellent octane improver for gasoline. U. K. Patent Application GB 2,123,411 describes a process for making a mixture of octane improving ethers by synthesizing an alcohol mixture containing methanol, ethanol, and higher alcohols and dehydrating the higher alcohols and etherification.

Because of the large amount of methanol available and its problems as a gasoline additive, processes which convert methanol to effective gasoline additives are valuable. Well-known is the Mobil process for converting methanol to gasoline-range hydrocarbons over an aluminum-containing molecular sieve. Little work has been reported on effectively converting methanol to higher alcohols, in particular, isobutanol.

Now a material has been found which allows a continuous, vapor phase, catalytic Guerbet-type of condensation to be effected on a large variety of different alcohols, their dehydration products (olefins), aldehydes, ethers and their mixtures. In particular, a catalyst effective in continuously converting a mixture of alcohols or their olefinic dehydration products such as methanol and ethanol, methanol and ethylene, methanol and propylene, or a mixture of methanol, formaldehyde, and ethanol in a continuous vapor phase process to higher alcohols has been found which can produce a substantial percentage of isobutanol in the product. Such a catalyst allows the production of MTBE using exclusively synthesis gas as the source of carbon to the process.

SUMMARY OF THE INVENTION

The invention described herein is a continuous vapor phase process to convert a feed comprising one or more $C_2$ or higher olefin in combination with methanol to at least one higher molecular weight alcohol which comprises contacting said one or more $C_2$ or higher olefin in combination with methanol in the vapor phase with a catalyst which is essentially magnesium oxide under condensation conditions to form a mixture containing said at least one or more higher molecular weight alcohol.

DETAILED DESCRIPTION OF THE INVENTION

The $C_2$ or higher alcohols useful herein are $C_2$ to $C_{20}$ alcohols such as ethanol, a propanol, a butanol, a pentanol, a hexanol, a nonanol, a dodecanol, and the like. The only limitation on such alcohols is their ability to be vaporized and passed over the catalyst at a temperature low enough to avoid substantial decomposition. The $C_2$ or higher olefins useful herein are $C_2$ to $C_{12}$ olefins such as ethylene, propylene, 1-and 2-butene, etc. Preferably the $C_2$ or higher olefin is ethylene or propylene. Most preferably, it is ethylene. Such feeds can also contain one or more $C_1$ to $C_4$ aldehydes or one or more $C_1$ to $C_6$ ethers.

The $C_1$ to $C_4$ aldehydes and $C_1$ to $C_6$ ethers generally include aldehydes and ethers such as formaldehyde, acetaldehyde, propionaldehyde, dimethyl ether, diethyl ether, methyl ethyl ether, methyl isopropyl ether, and the like. An especially preferred feed is a mixture of methanol, ethylene, and acetaldehyde, a mixture of methanol and ethylene, a mixture of methanol, ethylene, and propylene, or a partially separated effluent from a olefins unit combined with methanol. The feed to the process may in addition contain small amounts of one or more of methane, oxygen, nitrogen, hydrogen, carbon monoxide and carbon dioxide.

In general, after the feed is passed over the catalyst it will contain a mixture of alcohols at least one of which is of higher molecular weight than any of the starting alcohol or olefin. For example, a mixture of methanol and ethanol and a mixture of methanol, formaldehyde and ethanol produces at least 1-propanol, and a mixture of methanol, ethanol, and 1-propanol produces at least isobutanol; a mixture of methanol and isopropanol produces at least 2-butanol; ethanol alone produces at least n-butanol; n-butanol alone produces at least 2-ethylhexanol, and propanol alone produces at least 2-methylpentanol. Small amounts of non-alcohol products such as aldehydes, ethers and ketones generally also occur in the product.

A mixture of methanol and ethylene produces n-propanol, i-butyl alcohol and isomeric $C_4$ aldehydes, and a mixture of methanol and propylene produces similar products.

The magnesium oxide component useful in the catalyst herein described is essentially magnesium oxide. The magnesium oxide is present as more than about 80, more preferably more than about 90, and most preferably, more than about 95 wt. % of the total catalyst weight. The catalyst may also contain minor amounts of magnesium hydroxide, or alkaline materials such as a Period Group Ia or Group IIa compound including oxides and hydroxides. The magnesium oxide component is preferably of higher surface area, more preferably of surface area greater than about 25 sq m/g, and most preferably, of surface area above about 50 sq m/g, as measured by the BET method with nitrogen.

The magnesium oxide can be made by calcination of magnesium hydroxide or another magnesium compound such as magnesium carbonate or acetate. The preferred magnesium compound is magnesium hydroxide. The calcination temperature of the magnesium compound used should not be greatly in excess of the temperature needed to produce the oxide as the oxide can be produced in a less active form.

The catalyst may be used neat, but can be admixed with a diluent such as zirconia, titania, boria, alumina, and, particularly, a carbonaceous material such as charcoal and the like. Such diluents need not be completely inert and, indeed, it appears that the use of charcoal as a diluent improves certain of the condensation reactions described herein such as that of a mixture of methanol and ethanol, and a mixture of methanol, ethanol and a propanol. The diluent and the magnesium oxide component may be admixed in proportions of from 100 wt. % magnesium oxide component and no diluent to about 10 wt. % magnesium oxide component and about 90 wt. % diluent. More preferably, the proportions may vary between about 80 wt. % magnesium oxide component and about 20 wt. % diluent to about 20 wt. % magnesium oxide component and about 30 wt. % diluent.

The magnesium oxide component may in addition be supported on such supports as titania, alumina, silica, boria, zirconia, and a carbonaceous material such as charcoal and the like, by impregnation or otherwise. Magnesium oxide component/support wt. % ratios are generally the same as described above for catalysts wherein the magnesium oxide component is admixed with a diluent.

Use of a carrier gas mixed with the feed to the process can be advantageous. Such materials as hydrogen, carbon monoxide, carbon dioxide, a hydrocarbon, and inert gases such nitrogen, argon, and the like may be used to improve the condensation reaction. The use of hydrogen in the process can improve selectivity in the reaction of methanol with another alcohol and, if used, is generally employed in a hydrogen/feed ratio of from about 20:1 to about 1:1, more preferably, about from 10:1 to about 1:1.

The catalyst, with or without a carrier gas added to the feed, can be used in a fixed bed, ebullated bed, fluidized bed, or other type of vapor phase process. A copper-walled reactor has been found to be beneficial. In general, the temperature range useful in carrying out the condensation reaction described herein runs between about 300° and about 700° C., more preferably, between about 300° and about 500° C., and most preferably, between about 325° and about 450° C. The range of total reactor pressure useful in this invention runs between subatmospheric and about 1000 psig, more preferably, between subatmospheric and about 600 psig, and most preferably, subatmospheric to about 500 psig. Useful weight hour space velocities run between about 0.05 and about 60 $hr^{-1}$, and more preferably, between about 0.05 and about 10 $hr^{-1}$, based upon the magnesium oxide component in the catalyst.

. A particularly useful process which may be carried out employing the condensation reaction is the production of MTBE from synthesis gas as the sole carbon source. In such a process, synthesis gas is converted to methanol which is converted, for example, by carbonylation to ethanol. The ethanol is then condensed using a condensation catalyst such as the one disclosed herein with methanol to form a mixture rich in isobutanol. Other catalysts may also be used. The isobutanol may then be separated from the mixture, dehydrated, and reacted with additional methanol to form MTBE. One possible process of accomplishment production of MTBE is set out below to illustrate this use. The description of such process is not meant to limit the invention in any way.

EXAMPLES

General

Mixture of Alcohols

Mixtures of alcohols were evaluated in a fixed bed, continuous, down flow, stainless steel reactor. For some of the studies the stainless steel reactor was equipped with either a quartz or a copper liner. The catalyst was ground to 12/20- mesh size and physically mixed with bed diluent, charcoal, or alumina of the same mesh size. The catalyst bed was centered in the reactor with an inert alumina balls baffle above and below it for improved heat transfer. The alumina balls were kept at a lower temperature than the catalyst bed. The unit was pressured with helium unless otherwise noted and the catalyst brought to reaction temperature in flowing helium, at which time the alcohol was introduced via a Ruska pump.

Products were analyzed by three gas chromatographic systems. The fixed gases, CO and $CO_2$ along with $CH_4$ were analyzed by an on-line Hewlett-Packard 5730 gas chromatograph equipped with a thermal conductivity detector and a Chromosorb 106 packed column. Analysis was accomplished by using an external standard calibrated for CO, $CO_2$ and $CH_4$. The noncondensible light gases, $C_1$-$C_6$, were analyzed off-line using a flame ionization detector and a 6 ft N-octane Porosil C column. The peaks were identified and measured by matching retention times with an external standard containing $C_1$-$C_6$ hydrocarbons.

The condensible materials were collected in a bomb and analyzed with a flame ionization detector equipped with a 30 m capillary column of fused silica containing RSL 160 liquid phases. Peaks were identified by matching retention times of known alcohols, aldehydes, esters, ketones, olefins and paraffins. Many smaller peaks were not identified. The results are expressed in relative weight percents.

The condensible liquids were also measured on a Hewlett-Packard 5730 gas chromatograph equipped with a thermal conductivity detector. A 6 ft X⅛ in Poropak QS column, 80/100 mesh particles, was used. This system gave semiquantitative results for water, $C_1$-$C_6$ alcohols, and some of the lower molecular weight aldehydes, ketones and esters.

Mixtures of an Olefin and Methanol

In all cases methanol and/or other liquid reactants were metered by use of a syringe pump into a preheat zone of a quartz microreactor which was electrically heated and operated at atmospheric pressure. Ethylene or nitrogen carrier gas was metered into the top of the downflow reactor by use of Brooks Mass-flow Controllers. Liquid product was collected in a U-tube receiver chilled to −78° C. with a dry-ice isopropyl alcohol cooling bath in most cases or to 0° C. with an ice bath during those cuts when a gas sample was being taken. In all cases the catalyst volume was 9.4 cc.

Magnesium oxide catalyst was prepared by drying and calcination of 450° C. of firm homogeneous paste prepared from commercial magnesium hydroxide and distilled water. Additional catalyst components were incorporated into the paste either as solid hydroxides or soluble salts.

EXAMPLE 1

Magnesium oxide was prepared from 25 kg of commercially available magnesium hydroxide (VWR Scientific, Inc. reagent grade powder) by first mixing with 2000 g of distilled water and extruding the mass through a ⅛ in die plate. The extrudate was dried overnight at 120° C. and calcined first at 300° C. for 1 hr and then 450° C. for 12 hr. The resulting MgO having a BET surface area of 29 $M^2/g$ was used for Examples 2-6.

EXAMPLE 2

A 3.23 g (5 ml) quantity of magnesium oxide was mixed with 29 ml of charcoal supplied by Sargent-Welch as the catalyst. A 3/1 methanol to ethanol reactor feed and a copper lined reactor were used for this Example.

TABLE 1

| | |
|---|---|
| Temperature °F. | 800 |
| Pressure | 150 psig |
| Helium Flow | 0.099 $ft^3/hr$ |
| WHSV ($hr^{-1}$) | 2.5 |
| Wt % Methanol Converted | 22.4 |
| Wt % Ethanol Converted | 99.5 |
| Wt % Selectivity (Water-Free Basis) of Products | |
| 1-Propanol | 8.3 |
| Isobutanol | 31.6 |
| 1-Butanol | 0 |
| t-Butanol | 5.4 |
| CO + $CO_2$ | 22.1 |
| Methane | 5.4 |
| Ethane + Ethylene | 3.1 |
| Propane | 6.5 |
| Propylene | 1.2 |
| $C_4$ Hydrocarbons | 4.3 |
| $C_5^+$ Hydrocarbons | 2.1 |
| Acetaldehyde | 0 |
| Other | 10.0 |

EXAMPLE 3

Alcohol conversion is a function of space velocity and diluent character for the reaction of ethanol and methanol was studied and the results are shown in Tables 2, 3 and 4 below. A 3/1 methanol to ethanol reactor feed composition was used.

TABLE 2

Conversion as a Function of Space Velocity and Bed Diluent in a Copper Reactor

| WHSV ($hr^{-1}$) | % Methanol Converted | | | % Ethanol Converted | | |
|---|---|---|---|---|---|---|
| | Neat | Charcoal | Alumina | Neat | Charcoal | Alumina |
| 0.6 | 9 | 41 | — | 35 | 100 | — |
| 2.5 | 3 | 22 | — | 21 | 99 | — |
| 4.1 | — | 3 | — | — | 43 | — |

TABLE 3

Conversion as a Function of Space Velocity and Bed Diluent in a Stainless Steel Reactor

| WHSV ($hr^{-1}$) | % Methanol Converted | | | % Ethanol Converted | | |
|---|---|---|---|---|---|---|
| | Neat | Charcoal | Alumina | Neat | Charcoal | Alumina |
| 0.6 | 32 | 99 | — | 54 | 99 | — |
| 2.5 | 9 | 82 | 32 | 25 | 100 | 59 |

TABLE 4

Conversion as a Function of Space Velocity and Bed Diluent in a Quartz Reactor

| WHSV (hr$^{-1}$) | % Methanol Converted | | | % Ethanol Converted | | |
|---|---|---|---|---|---|---|
| | Neat | Charcoal | Alumina | Neat | Charcoal | Alumina |
| 0.6 | 23 | 5 | — | 63 | 13 | — |
| 2.5 | 12 | 1 | — | 37 | 4 | — |

EXAMPLE 4

The effect of a bed diluent on product distribution in a copper-lined reactor for the reaction of ethanol and methanol is given in Table 5 below. A 3/1 methanol to ethanol reactor feed was used.

TABLE 5

Effect of Bed Diluent on Product Selectivity in a Copper Reactor

| Bed Diluent | None | Charcoal |
|---|---|---|
| Temperature °F. | 800 | 800 |
| WHSV (hr$^{-1}$) | 2.5 | 2.5 |
| Wt % Methanol Converted | 3.3 | 22.4 |
| Wt % Ethanol Converted | 21.4 | 99.5 |
| Wt % Selectivity (Water-Free Basis) of Products | | |
| 1-Propanol | 35.4 | 8.3 |
| Isobutanol | 2.5 | 31.6 |
| 1-Butanol | | |
| t-Butanol | | 5.4 |
| CO + CO$_2$ | 14.2 | 22.1 |
| Methane | 1.5 | 5.4 |
| Ethane + Ethylene | 3.1 | 3.1 |
| Propane | 0 | 6.5 |
| Propylene | 0.7 | 1.2 |
| C$_4$ Hydrocarbons | 0 | 4.3 |
| C$_5^+$ Hydrocarbons | 0 | 2.1 |
| Acetaldehyde | 17.8 | 0 |
| Other | 17.5 | 10.0 |

EXAMPLE 5

The effect of a bed diluent on product distribution on the reaction of ethanol and methanol in a quartz reactor is given below in Table 6. A 3/1 methanol to ethanol reactor feed was used.

TABLE 6

Effect of Bed Diluent on Product Selectivity in a Quartz Reactor

| Bed Diluent | None | Charcoal |
|---|---|---|
| Temperature °F. | 800 | 800 |
| WHSV (hr$^{-1}$) | 0.6 | 0.6 |
| Wt % Methanol Converted | 23.5 | 5.3 |
| Wt % Ethanol Converted | 62.5 | 13.4 |
| Wt % Selectivity (Water-Free Basis) of Products | | |
| 1-Propanol | 0 | 0 |
| Isobutanol | 0 | 0 |
| 1-Butanol | 0 | 0 |
| t-Butanol | 0 | 0 |
| CO + CO$_2$ | 41.8 | 29.6 |
| Methane | 4.0 | 5.9 |
| Ethane + Ethylene | 2.2 | 3.1 |
| Propane | 0.2 | 9.3 |
| Propylene | 0.6 | 0 |
| C$_4$ Hydrocarbons | 0.1 | 2.3 |
| C$_5^+$ Hydrocarbons | 0.1 | 0 |
| Acetaldehyde | 49.5 | 49.8 |
| Other | 1.5 | 0 |

EXAMPLE 6

The effect of differing bed diluents on the reaction of methanol and ethanol in a stainless steel reactor is given below in Table 7. A 3/1 methanol to ethanol reactor feed was used.

TABLE 7

Effect of Bed Diluent on Product Selectivity in a Stainless Steel Reactor

| Bed Diluent | None | Charcoal | Alumina |
|---|---|---|---|
| Temperature °F. | 800 | 800 | 800 |
| WHSV (hr$^{-1}$) | 2.5 | 2.5 | 2.5 |
| Wt % Methanol Converted | 7.6 | 90.6 | 29.0 |
| Wt % Ethanol Converted | 20.4 | 99.1 | 54.6 |
| Wt % Selectivity (Water-Free Basis) of Products | | | |
| 1-Propanol | 21.1 | 0.1 | 3.0 |
| Isobutanol | 0 | 0.8 | 0 |
| 1-Butanol | 0 | 0 | 0 |
| t-Butanol | 0 | 0 | 0 |
| CO + CO$_2$ | 35.8 | 67.7 | 57.6 |
| Methane | 10.2 | 12.6 | 6.9 |
| Ethane + Ethylene | 5.6 | 5.4 | 2.7 |
| Propane | 0.1 | 2.0 | 0.3 |
| Propylene | 0.8 | 3.4 | 2.5 |
| C$_4$ Hydrocarbons | 0 | 2.5 | 0.4 |
| C$_5^+$ Hydrocarbons | 0.2 | 1.8 | 0.5 |
| Acetaldehyde | 9.4 | 0.3 | 18.2 |
| Other | 16.6 | 3.3 | 7.7 |

EXAMPLE 7

A 500 g portion of magnesium hydroxide powder supplied by Sargent-Welsh was placed in a beaker, treated with water to make a thick paste and then dried at 130° C. A first portion of it was calcined at 450° C. for 12 hr and a second portion was calcined at 538° C. for 12 hr. The latter material shows a pore volume of 0.9793 cc/g, an average pore radius of 197 Å, and a BET (nitrogen) surface area of 90 m$^2$/g. Both calcination products were crushed and sieved to 18/40 mesh granules.

EXAMPLE 8

Both MgO products of Example 7 were loaded into a quartz reactor, and a 3/1 methanol to ethanol feed passed over the catalyst for 1 hr at 450° C. The results are set out below in Table 8.

TABLE 8

Effect of Calcination Temperature on Product Distribution

| Component | 538° C. Product (%) | 450° C. Product (%) |
|---|---|---|
| acetaldehyde | 0.75 | * |
| propionaldehyde | 0.59 | * |
| isobutyraldehyde + acetone | 0.47 | 1.48 |
| methanol | 50.6 | 36.11 |
| ethanol | 17.4 | 3.66 |
| n-propanol | 10.3 | 5.68 |
| isobutanol | 7.63 | 29.4 |
| allyl alcohol | 1.0 | * |
| n-butanol | 1.78 | 0.62 |
| 2-Me-1-butanol | 3.13 | 6.35 |

*not measured

EXAMPLE 9

A 73.58 g portion of Al(NO$_3$)$_3$.9 H$_2$O was dissolved in 140 g of water. A 130.25 g portion of magnesium hydroxide was slowly added to the solution until a solid paste was formed. Additional water and the remaining hydroxide were added until the thick paste was again formed. The paste was dried at 121° C. and calcined 12 hr at 538° C. The product catalyst contains about 10 wt. % aluminum oxide.

EXAMPLE 10

A 5/1 methyl alcohol/diethyl ether mixture (0.0126 ml/min of mixture, 6 ml/min of nitrogen) was passed over 9.4 ml of catalyst in a quartz reactor at 430° C. and ambient pressure for 140 min giving 0.94 g of liquid product in a dry ice-isopropanol trap. The product distribution is given below in Table 9.

TABLE 9

| Liquid Product Component | Wt. % |
|---|---|
| methyl ether | 5.79 |
| methyl ethyl ether | 3.62 |
| diethyl ether | 41.7 |
| methyl n-propyl ether | 1.53 |
| methyl isobutyl ether | 2.41 |
| propionaldehyde | 0.67 |
| isobutyraldehyde - acetone | 0.84 |
| methanol | 31.4 |
| ethanol | 4.51 |
| n-propanol | 2.21 |
| isobutanol | 4.62 |
| 2-Me-1-butanol | 0.27 |

EXAMPLE 11

A 2/1 methanol/n-butanol mixture (0.0126 ml/min of mixture, 6 ml/min of nitrogen) was passed over the 538° C. calcined MgO catalyst of Example 7 at 425° C. and ambient pressure for 60 min given 0.77 g of liquid product in a dry ice-isopropanol trap. The product distribution is shown in Table 10 below:

TABLE 10

| Liquid Product Component | Wt. % |
|---|---|
| methyl alcohol | 24.7 |
| isopropanol | 0.88 |
| n-butanol | 45.8 |
| 2-Me-1-butanol | 19.3 |
| 2-Me-1-pentanol | 1.54 |

EXAMPLE 12

Ethanol (0.0126 ml/min, 6 ml/min of nitrogen) was passed over the 538° C. calcined magnesium oxide of Example 7 at 425° C. and ambient pressure for 105 min giving 0.82 g of liquid product trapped in a dry ice-isopropanol trap. The product distribution is shown below in Table 11.

TABLE 11

| Liquid Product Component | Wt. % |
|---|---|
| acetaldehyde | 1.4 |
| propionaldehyde | 0.6 |
| 1-butyraldehyde + acetone | 0.78 |
| n-butyraldehyde | 0.6 |
| methanol | 1.7 |
| 2-butanone | 0.87 |
| 2-propanol | 2.4 |
| ethanol | 39.6 |
| methyl vinyl keton | 0.9 |
| 2-pentanone | 1.2 |
| 2-butanol | 1.0 |
| n-propanol | 1.0 |
| crotonaldehyde | 0.67 |
| allyl alcohol | 1.59 |
| mesityl oxide | 0.48 |
| n-butanol | 14.8 |
| 2-methyl-1-butanol | 0.78 |

EXAMPLE 13

A 5/1/1 methanol, ethanol, and 1-propanol mixture (0.0126 ml/min, 6 ml/min of nitrogen) was passed over the 538° C. calcined magnesium oxide of Example 7 at 425° C. and ambient pressure for 120 min giving 1.36 g of liquid product trapped in a dry ice-isopropanol trap. The product distribution is shown in Table 12.

TABLE 12

| Liquid Product Component | Wt. % |
|---|---|
| acetaldehyde | 0.67 |
| methyl n-propyl ether | 0.98 |
| ethyl n-butyl ether | 1.17 |
| isobutyraldehyde + acetone | 1.35 |
| methanol | 37.4 |
| ethanol | 6.74 |
| i-propanol | 13.2 |
| i-butanol | 24.1 |
| 2-Me-1-butanol | 2.04 |
| 2-Me-1-pentanol | 2.19 |

EXAMPLE 14

Various mixtures of olefins and methanol in a $N_2$ stream were passed over magnesium oxide catalysts and the products of the reaction determined as set out above. The magnesium oxide catalysts were made by drying and calcining at 450° C. a firm homogeneous paste prepared from commercial magnesium hydroxide and distilled water. Additional components such as silver metal and alumina.

The catalytic results are shown below in Table 13 below. Wt. % yield of the reaction products is equal to wt. % selectivity x the estimated conversion of methanol in wt. % as determined by gas-liquid chromatography. A mixture of water and ethylene over the same catalyst yielded no organic products which is evidence that olefin hydration and then condensation does not occur over magnesium oxide.

TABLE 13

Reaction of MeOH with Ethylene or Propylene over MgO Compositions

| Olefin[1] Feed | Reac. T. (°C.) | Est. Conv. MeOH (wt. %) | Yield (Wt. %) | | | | | |
|---|---|---|---|---|---|---|---|---|
| | | | A[5] | B[6] | C[7] | D[8] | E[9] | F[10] |
| $C_2$ | 425 | 1.22 | 0.03 | | 0.34 | | | |
| | 425 | 1.28 | 0.05 | | 0.54 | | | |
| | 425 | 1.69 | 0.07 | | 0.70 | 0.02 | | |
| | 435 | 3.41 | 0.30 | 0.40 | 2.48 | 0.06 | | |
| | 425 | 4.11 | 0.25 | 0.06 | 3.59 | 0.08 | | |
| $C_2^2$ | 425 | 0.85 | 0.05 | | 0.60 | | | |
| | 425 | 1.41 | 0.04 | 0.03 | 0.60 | | | |
| | 425 | 1.46 | 0.04 | 0.03 | 0.60 | | | |
| | 435 | 1.52 | 0.10 | 0.04 | 1.09 | | | |
| $C_2^3$ | 425 | 4.84 | 0.50 | 0.07 | 3.70 | 0.05 | | |
| | 425 | 6.93 | 0.05 | 0.09 | 5.65 | 0.09 | | |
| | 435 | 10.68 | 1.05 | 0.11 | 9.08 | 0.14 | | |
| $C_3$ | 435 | 4.59 | 0.11 | | 1.07 | 0.3 | | |
| | 435 | 3.30 | 0.12 | | 1.27 | 0.37 | | |
| | 435 | 4.10 | 0.12 | | 1.30 | 0.37 | | |
| | 435 | 3.50 | 0.12 | | 1.45 | 0.42 | | |
| | 435 | 6.45 | 0.27 | 0.03 | 2.20 | 0.54 | | |
| | 435 | 14.04 | 2.15 | 0.09 | 9.01 | 1.23 | | |
| $C_3$ | 425 | 7.46 | 0.15 | 0.03 | 1.86 | 0.80 | | |
| | 425 | 6.68 | 9.15 | | 1.72 | 0.73 | | |
| | 435 | 7.32 | 0.35 | 0.04 | 3.31 | 1.28 | | |
| $C_2^3$ | 425 | 9.38 | 3.54 | 0.11 | 2.24 | 0.18 | | |
| | 425 | 6.62 | 1.05 | 0.22 | 2.46 | 0.21 | | |
| | 425 | 4.44 | 0.56 | 0.17 | 2.06 | 0.16 | | |
| | 435 | 6.76 | 0.77 | 0.20 | 3.71 | 0.28 | | |
| $C_2^4$ | 425 | 11.39 | | 0.15 | 0.13 | | 0.19 | 0.16 |
| | 425 | 7.47 | | 0.28 | 0.24 | | 0.11 | 0.20 |
| | 425 | 8.88 | | 0.36 | 0.37 | | 0.13 | 0.20 |

TABLE 13-continued

Reaction of MeOH with Ethylene or Propylene over MgO Compositions

| Olefin[1] Feed | Reac. T. (°C.) | Est. Conv. MeOH (wt. %) | Yield (Wt. %) | | | | | |
|---|---|---|---|---|---|---|---|---|
| | | | A[5] | B[6] | C[7] | D[8] | E[9] | F[10] |
| | 400 | 13.38 | | 0.30 | 0.25 | | 0.16 | 0.14 |

[1] olefin/methanol feed ratio is 2.71/1 for all runs
[2] 5% water in feed
[3] 95% MgO and 5% Ag
[4] 90% MgO and 10% $Al_2O_3$
[5] i-$C_4$ aldehyde
[6] n-prOH
[7] i-$C_4$OH
[8] 2-Me-1-BuOH
[9] $C_2$ Aldehyde
[10] EtOH That which is claimed is:

1. A continuous vapor phase process to convert a feed comprising a $C_2$ or higher olefin in combination with methanol to at least one higher molecular weight alcohol which comprises contacting said $C_2$ or higher olefin in combination with methanol in the vapor phase with a catalyst which is essentially magnesium oxide under condensation conditions to form a mixture containing said at least one higher molecular weight alcohol.

2. The process of claim 1 wherein said catalyst contains said magnesium oxide admixed with a diluent.

3. The process of claim 2 wherein said feed comprises a mixture of methanol and ethylene, a mixture of methanol, formaldehyde and ethylene, a mixture of methanol, ethylene, and propylene or a mixture of methanol and propylene.

4. The process of claim 1 wherein said catalyst which is essentially magnesium oxide additionally contains a promoter selected from the group consisting of Periodic Group Ia and IIa metals and compounds.

5. The process of claim 1 wherein said catalyst is magnesium oxide made by the thermal decomposition of magnesium hydroxide, said magnesium oxide exhibiting a surface area above 50 sq. m/g.

6. The process of claim 5 wherein said feed comprises a mixture of methanol and ethylene, a mixture of methanol, formaldehyde and ethylene, a mixture of methanol, ethylene, and propylene or a mixture of methanol and propylene.

* * * * *